United States Patent [19]

Fidler

[11] Patent Number: 4,774,085
[45] Date of Patent: Sep. 27, 1988

[54] PHARMACEUTICAL ADMINISTRATION SYSTEMS CONTAINING A MIXTURE OF IMMUNOMODULATORS

[75] Inventor: Isaiah J. Fidler, Kingwood, Tex.

[73] Assignee: 501 Board of Regents, Univ. of Texas, Austin, Tex.

[21] Appl. No.: 753,192

[22] Filed: Jul. 9, 1985

[51] Int. Cl.[4] .................. A61K 45/02; C12P 21/00
[52] U.S. Cl. ................................. 424/85.5; 435/68
[58] Field of Search .................................. 424/85

[56] References Cited

U.S. PATENT DOCUMENTS

4,522,811  6/1985  Eppstein et al. .................. 424/85

OTHER PUBLICATIONS

Saiki et al., Cancer Research, vol. 45, pp. 6188–6193, 1985.
Chemical Abstracts, vol. 104, Abstract No. 18480g, 1986.
Chemical Abstracts, vol. 103, Abstract No. 52561y, 1985.
Journal of Immunology, 131, No. 6. Dec. 1983, pp. 2821–2825.
Journal of Immunology, 125, No. 6. Dec. 1980, pp. 2454–2460.
Cancer Research, 39, Mar. 1979, pp. 881–892.
Journal of Clinical Investigation, 72, Jul. 1983, pp. 304–315.

Primary Examiner—Blonde L. Hazel
Attorney, Agent, or Firm—Bruce M. Collins

[57] ABSTRACT

The present invention relates to pharmaceutical administration systems containing phosphatidylserine and phosphatidylcholine or phosphatidylethanolamine derivatives in the form of liposomes which encapsulate water soluble muramyldipeptide derivatives in combination with gamma-interferon. The liposomes are prepared by conventional dispersion methods. The pharmaceutical administration systems when applied in the form of liposomes are especially useful in the cancer chemotherapy for combating metastatic tumor cells.

8 Claims, No Drawings

PHARMACEUTICAL ADMINISTRATION SYSTEMS CONTAINING A MIXTURE OF IMMUNOMODULATORS

The present invention relates to pharmaceutical administration systems consisting of immunomodulators and phospholipids, a process for the preparation of these administration systems and their method of use.

List of Abbreviations

AM: Alveolar macrophages
BSA: Bovine serum albumine
CSA: Colony stimulating activity
ULV: Unilamellar vesicles
MLV: Multilamellar liposomes
MDP: N-acetyl-D-muramyl-L-alanyl-D-isoglutamine
nor-MDP: N-acetyldesmethylmuramyl-L-alanyl-D-isoglutamine Immunomodulators having immunostimulating action and their potential use in cancer chemotherapy are subject matter of various publications.

Immunomodulators of the muramylpeptide-type are known, for example, from the British Patent Specification No. 1,570,625 and U.S. Pat. No. 4,406,890 and their immunostimulating or immunopotentiating effect has been established in vitro in various assays, for example assay of AM-mediated cytotoxicity, S. Sone and I. J. Fidler, J. Immun. Vol. 125, 6, 2454–2460 and the references cited therein, or in vitro, for example by increasing the antibody production against BSA, Freund's complete adjuvant, liberating large amounts of CSA from mouse-macrophages, or increasing the survival rate of mice infected by Ehrlich tumor cells.

Immunomodulators of the gamma-interferon or immune interferon type and their isolation or preparation have been described in numerous patent specifications. Natural and recombinant immune interferon shows an activating effect on human monocyte cytotoxicity, J. Le et al., J. Immunol. Vol. 131, 6, 2821–2826.

The phospholipids in the pharmaceutical administration system of the present invention are dispersed in the form of liposomes.

Liposomes have been described in the literature in numerous publications. Their structure and use has been made subject matter of intensive research work. Depending on their shell structure, a distinction is made between unilamellar liposomes or vesicles (ULV) and multilamellar liposomes or vesicles (MLV). In some publications, the term "vesicle" strictly applies to unilamellar liposomes. ULV are having a spherical shell consisting of one double layer of lipids, especially phospholipids, and MLV a spherical shell consisting of several double layers arranged in an onion-shell like pattern.

The spherical shell may consist of phospholipids such as phosphatidylcholine, phosphatidylethanolamine or phosphatidic acid and optionally "neutral" lipids such as cholesterol. This shell encapsulates an internal volume containing the aqueous phase and pharmacologically active compounds.

Depending upon the degree of lipophily and other parameters, such as temperature or concentration, the encapsulated compounds are present in the enclosed aqueous phase and/or in the double layer(s).

There exists a great deal of interest in the therapeutic or diagnostic use of liposomes as carriers of active ingredients of widely varied kinds. Accordingly, liposomes have been proposed as carriers for proteins, for example antibodies, or enzymes, hormones, vitamins, or, for analytical purposes, as carriers for compounds labelled by radioactive isotopes. For example, in the U.S. Pat. No. 3,993,754 a chemotherapeutic process is disclosed which is useful for the treatment of tumor cells by using liposomes as carriers.

Pharmaceutical administration systems based on liposomes have been described in the general review issued by G. Gregoriadis, Liposome Technology, Vol. II, Incorporation of Drugs, Proteins and Genetic Material, CRC Press 1984. Such systems have the advantage that biologically active material can be introduced into tissues by phagocytosis, especially into tissues of the reticulo-endothelial system. For example, a transport mechanism is known how antibiotics are being introduced into infected tissues by phagocytosis thus causing the improved removal or destruction of the infecting microorganism. Endocytosis also is a helpful mechanism in the combat of centres of inflammation. Antirheumatic pharmaceuticals encapsulated in liposomes are preferably introduced into infected tissues as compared to "healthy" tissues. Moreover, cytostatic agents, commonly known as "anticancer drugs", can be introduced into specific organs of the reticulo-endothelial system (liver, spleen or marrow). Additionally, due to filtration in the capillaries of the lung and subsequent transport by migrating monocytes, biologically active material, for example compounds having immunomodulatory properties, can be concentrated in alveolar macrophages. This results in an improved action on metastatic lung tumours and in a simultaneous reduction of toxicity.

Liposome encapsulated compounds having immunomodulatory properties may effect changes of the responses of the immune system (immune stimulation or suppression). For example, G. Poste et al. report the activation of cytotoxic properties against tumor cells of mouse macrophages by liposome encapsulated lymphokines, see Cancer Research 39, 881 (1979). S. Sone and I. Fidler report the in-vitro activation of cytotoxic activities of alveolar macrophages in rats by muramyl-dipeptides encapsulated in liposomes, see Cell. Immunol. 57, 42 (1981).

A tumoricidal activity of human monocytes activated in vitro by free and liposome encapsulated human lymphones, for example macrophage activating factor (MAF), has been reported by E. S. Kleinerman et. al., J. of Clin. Invest. Vol. 72, 304–315 (1983).

Object of the present invention are pharmaceutical administration systems whose components, when applied in the form of liposomes, are being enriched or concentrated in the lung and/or liver followed by endocytosis of the macrophages and, therefore, activate the cells of monocytes or macrophages, for example alveolar or peritoneal macrophages. It has been found that liposomes consisting of phospholipids and a muramyl-dipeptide in combination with gamma-interferon improve the activation of macrophages as compared to liposomes containing a muramyldipeptide or liposomes containing gamma-interferon.

The present invention relates to pharmaceutical administration systems consisting of
(a) a water soluble muramylpeptide,
(b) gamma-interferon,
(c) a phospholipid of the formula

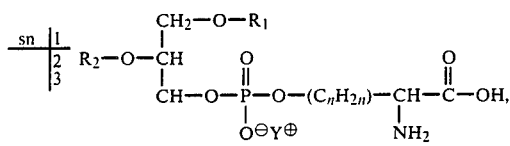

(I)

wherein n is one, two or three, $R_1$ and $R_2$ independently of each other represent alkyl, alkenyl or acyl each having 10-20 carbon atoms, and $Y^\oplus$ is the cation of a pharmaceutically acceptable base,
(d) a phospholipid of the formula

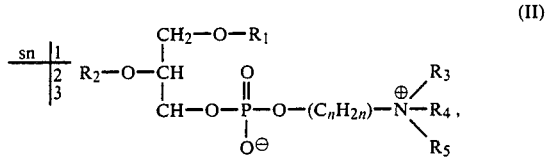

(II)

wherein n is two, three or four, $R_1$ and $R_2$ are defined as above and $R_3$, $R_4$ and $R_5$ represent hydrogen or $C_1$-$C_4$-alkyl, and, optionally, a pharmaceutically acceptable carrier solution buffered to pH 7.0-7.8 and, optionally, pharmaceutically acceptable carriers in solid form.

In the context of the description of the present invention, the general terms employed hereinbefore and hereinafter preferably have the following meanings:

The terms "lower" used in connection with organic radicals, for example lower alkyl, lower alkylene, lower alkoxy, lower alkanoyl, etc., means that such organic radicals, unless expressly defined otherwise, contain up to 7, preferably up to 4, carbon atoms.

The nomenclature of the phospholipids of the formulae I and II is in agreement with the recommendations of the IUPAC and IUB Commission on Biochemical Nomenclature (CBN) according to the Eur. J. of Biochem. 79, 11-21 (1977) "Nomenclature of Lipids" (sn-nomenclature, stereospecific numbering).

A water soluble muramylpeptide (component (a)) is preferably a muramyldipeptide of the formula

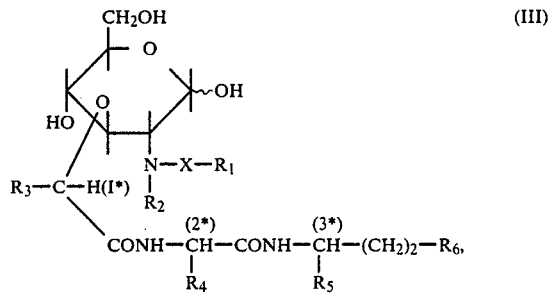

(III)

wherein X represents the groups —C(=O)— or —C(=O)—O—, $R_1$ represents $C_1$-$C_4$-alkyl, $R_2$, $R_3$ and $R_4$ independently of each other represent hydrogen or $C_1$-$C_4$-alkyl and $R_5$ and $R_6$ independently of each other represent carbamoyl, carboxy or esterified carboxy or a pharmaceutically acceptable salt thereof.

In a muramylpeptide of the formula III $R_1$, $R_2$, $R_3$ and $R_4$ defined as $C_1$-$C_4$-alkyl are, for example, ethyl, n-propyl or isopropyl or, preferably, methyl.

Esterified carboxy $R_5$ or $R_6$ is, for example, methoxy- or ethoxycarbonyl.

Pharmaceutically acceptable salts of compounds of the formula III are formed, for example, by compounds of the formula III having an acidic group, for example a carboxy group, and are especially alkali metal salts, such as sodium or potassium salts. Other parmaceutically acceptable salts are formed with organic amines, such as optionally hydroxy-substituted mono-, di- or tri-alkylamines, for example diethylamine, di-(2-hydroxyethyl)-amine, triethylamine, N,N-dimethyl-N-(2-hydroxyethyl)-amine, tri-(2-hydroxyethyl)-amine or N-methyl-D-glucamine.

The 1*-carbon atom has R- (or D-) configuration if $R_3$ denotes $C_1$-$C_4$-alkyl. The 2*-carbon atom has the S- (or L-) configuration if $R_4$ denotes $C_1$-$C_4$-alkyl. The 3*-carbon atom has the R- or the S-(D,L-) configuration. Preferred are compounds wherein the 3*-carbon atom has the R- (or D-) configuration.

Preferred are muramylpeptides of the formula III wherein X represents the group —C(=O)—, $R_1$ is methyl, $R_2$ is hydrogen, $R_3$ and $R_4$ are hydrogen or methyl, $R_5$ is carbamoyl and $R_6$ is carboxy, for example MDP or nor-MDP and the sodium salts thereof.

Gamma-interferon (component b))—or immune interferon—is especially natural or recombinant human gamma interferon, especially human gamma-interferon obtainable according to the European Patent Application Nos. 63,482, 77,670, 83,777, 88,540, 89,676, 95,350, 99,084, 110,044 and 112,967 and the International PCT Application Nos. (WO) 83/04,053 or WO 84/02,129.

Preferred is human gamma-interferon of the following amino acid sequences:

H₂N—Cys—Tyr—Cys—Gln—Asp—Pro—Tyr—Val—Gln—
—Glu—Ala—Glu—Asn—Leu—Lys—Lys—Tyr—Phe—
—Asn—Ala—Gly—His—Ser—Asp—Val—Ala—Asp—
—Asn—Gly—Thr—Leu—Phe—Leu—Gly—Ile—Leu—
—Lys—Asn—Trp—Lys—Glu—Glu—Ser—Asp—Arg—
—Lys—Ile—Met—Gln—Ser—Gln—Ile—Val—Ser—
—Phe—Tyr—Phe—Lys—Leu—Phe—Lys—Asn—Phe—
—Lys—Asp—Asp—Gln—Ser—Ile—Gln—Lys—Ser—
—Val—Glu—Thr—Ile—Lys—Glu—Asp—Met—Asn—
—Val—Lys—Phe—Phe—Asn—Ser—Asn—Lys—Lys—
—Lys—Arg—Asp—Asp—Phe—Glu—Lys—Leu—Thr—
—Asn—Tyr—Ser—Val—Thr—Asp—Leu—Asn—Val—
—Gln—Arg—Lys—Ala—Ile—His—Glu—Leu—Ile—
—Gln—Val—Met—Ala—Glu—Leu—Ser—Pro—Ala—
—Ala—Lys—Thr—Glu—Lys—Arg—Lys—Arg—Ser—
—Gln—Met—Leu—Phe—Gln—Gly—Arg—Arg—Ala—
—Ser—Gln—OH, according to the European Patent Application No. 121,157 and H₂N—Cys—Tyr—Cys—Gln—Asp—Pro—Tyr—Val—Lys—
—Glu—Ala—Glu—Asn—Leu—Lys—Lys—Tyr—Phe—
—Asn—Ala—Gly—His—Ser—Asp—Val—Ala—Asp—
—Asn—Gly—Thr—Leu—Phe—Leu—Gly—Ile—Leu—
—Lys—Asn—Trp—Lys—Glu—Glu—Ser—Asp—Arg—
—Lys—Ile—Met—Gln—Ser—Gln—Ile—Val—Ser—
—Phe—Tyr—Phe—Lys—Leu—Phe—Lys—Asn—Phe—
—Lys—Asp—Asp—Gln—Ser—Ile—Gln—Lys—Ser—
—Val—Glu—Thr—Ile—Lys—Glu—Asp—Met—Asn—
—Val—Lys—Phe—Phe—Asn—Ser—Asn—Lys—Lys—
—Lys—Arg—Asp—Asp—Phe—Glu—Lys—Leu—Thr—
—Asn—Tyr—Ser—Val—Thr—Asp—Leu—Asn—Val—
—Gln—Arg—Lys—Ala—Ile—His—Glu—Leu—Ile—
—Gln—Val—Met—Ala—Glu—Leu—Ser—Pro—Ala—
—Ala—Lys—Thr—Gly—Lys—Arg—Lys—Arg—Ser—
—Gln—Met—Leu—Phe—Arg—Gly—Arg—Arg—Ala—
—Ser—Gln—OH.

according to the British Patent Specification No. 2,107,718.

In a phospholipid of the formula I (component (c)) the group —$(C_nH_{2n})$— is straight chained or branched alkylene, for example 1,1- or 1,2-ethylene, 1,1-, 1,2- or 1,3-propylene or, preferably, methylene (n=1).

Alkyl $R_1$ and $R_2$ is preferably straight-chained with an even number from 10 to 20 carbon atoms, for example n-decyl, n-dodecyl (lauryl), n-tetradecyl (myristyl), n-hexadecyl (cetyl), n-octadecyl (stearyl) or n-icosyl (arachinyl).

Alkenyl $R_1$ and $R_2$ is preferably straight-chained with an even number from 12 to 20 carbon atoms and a double bond, for example 9-cis-dodecenyl (lauroleyl), 9-cis-tetradecenyl (myristoleyl), 9-cis-hexadecenyl (palmitoleinyl), 6-cis-octadecenyl (petroselinyl), 6-transoctadecenyl (petroselaidinyl), 9-cis-octadecenyl (oleyl), 9-transoctadecenyl (elaidinyl) or 9-cis-icosenyl (gadoleinyl).

Acyl $R_1$ and $R_2$ is preferably straight-chained with an even number of 10–20 carbon atoms, for example $C_{10}$–$C_{20}$-alkanoyl or $C_{10}$–$C_{20}$-alkenoyl.

Alkanoyl $R_1$ and $R_2$ is preferably n-decanoyl, n-dodecanoyl (lauroyl), n-tetradecanoyl (myristoyl), n-hexadecanoyl (palmitoyl), n-octadecanoyl (stearoyl) and n-icosanoyl (arachinoyl).

Alkenoyl $R_1$ and $R_2$ is preferably 9-cis-dodecenoyl (lauroleoyl), 9-cis-tetradecenoyl (myristoleoyl), 9-cis-hexadecenoyl (palmitoleoyl), 6-cis-octadecenoyl (petroseleoyl), 6-transoctadecenoyl (petroselaidoyl), 9-cis-octadecenoyl (oleoyl), 9-transoctadecenoyl (elaidoyl), 11-cis-octadecenoyl (vaccenoyl) and 9-cis-icosenoyl (gadoleoyl).

The cation $Y^\oplus$ of a pharmaceutically acceptable base is, for example, an alkali metal ion, for example the lithium, sodium or the potassium ion, the ammonium ion, a mono-, di- or tri-$C_1$–$C_4$-alkylammonium ion, for example the trimethyl-, ethyl-, diethyl-, or triethylammoniumion, a 2-hydroxyethyl-tri-$C_1$–$C_4$-alkylammoniumion, for example the choline cation, or is the 2-hydroxyethylammoniumion, or the cation of a basic aminoacid, for example lysine or arginine.

Preferred are phospholipids of the formula I from natural sources wherein $R_1$ and $R_2$ are different or identical $C_{10}$–$C_{20}$-alkanoyl or $C_{10}$–$C_{20}$-alkenoyl groups, for example n-dodecanoyl, n-tetradecanoyl, n-hexadecanoyl, or n-octadecanoyl, or 9-cis-dodecenoyl, 9-cis-tetradecenoyl, 9-cis-hexadecenoyl, 6-cis-, 6-trans-, 9-cis-, 9-trans- or 11-cis-octadecenoyl or 9-cis-icosenoyl, for example phosphatidylserine from bovine brain, and synthetic phospholipids of the formula I wherein $R_1$ and $R_2$ are identical $C_{10}$–$C_{20}$-alkenoyl groups, for example 9-cis-hexadecenoyl, 6-cis-, 6-trans-, 9-cis-, 9-trans- or 11-cis-octadecenoyl, for example sodium-1,2-di-(9-cis-octadecenoyl)-3-sn-phosphatidyl-(S)-serine.

In a phospholipid of the formula II (component (d)) the group —$(C_nH_{2n})$— is straight chain or branched alkylene, for example 1,1-, 1,2-, or 1,3-propylene or 1,2-, 1,3- or 1,4-butylene or, preferably, 1,2-ethylene (n=2).

In a phospholipid of the formula II the groups $R_3$, $R_4$ and $R_5$ preferably are hydrogen or methyl.

Preferred are phospholipids of the formula II, wherein $R_4$, $R_5$ and $R_6$ are hydrogen or methyl, from natural sources from plants or from animals, and wherein $R_1$ and $R_2$ are different or identical $C_{10}$–$C_{20}$-alkanoyl or $C_{10}$–$C_{20}$-alkenoyl groups, for example n-dodecanoyl, n-tetradecanoyl, n-hexadecanoyl, or n-octacedanoyl, or 9-cis-dodecenoyl, 9-cis-tetradecenoyl, 9-cis-hexadecenoyl, 6-cis-, 6-trans-, 9-cis-, 9-trans- or 11-cis-octadecenoyl, or 9-cis-icosenoyl, for example lecithin or cephalin from chicken eggs or soy bean lecithin, synthetic phospholipids (II) wherein $R_1$ and $R_2$ are identical $C_{10}$–$C_{20}$-alkanoyl groups, and synthetic phospholipids (II), wherein $R_1$ is $C_{10}$–$C_{20}$-alkanoyl, for example n-dodecanoyl, n-tetradecanoyl, n-hexadecanoyl, or n-octadecanoyl, and $R_2$ is $C_{10}$–$C_{20}$-alkenoyl, for example 9-cis-hexadecenoyl, 6-cis-, 6-trans-, 9-cis-, 9-trans- or 11-cis-octadecenoyl, especially 1-n-hexadecanoyl-2-(9-cis-octadecenoyl)-3-sn-phosphatidylcholine.

The pharmaceutical administration system according to the present invention is characterized by a synergistic action of the active components (a)—a muramyldipeptide—and (b)—gamma-interferon whenever these components in combination are encapsulated in liposomes consisting of the phopholipids (I) and (II). In general, an increased stimulation of the immune response has been observed when liposomes containing a conbination of the components (a) and (b) are administered as compared to liposomes containing the individual components (a) or (b). This effect is caused by an improved stimulation of macrophages by endocytosis of the liposomes enriched, for example, in lung, liver and spleen. A quick removal of metastatic tumor cells has been observed as shown in various assays in the Test Reports I and II of Example 5.

Therefore, the pharmaceutical administration system according to the present invention, when applied in the form of liposomes, is especially useful in the cancer chemotherapy for combating metastatic tumor cells.

Aqueous liposome dispersion wherein the phospholipids of the formulae I and II are the encapsulating material and muramylpeptide of the formula III in combination with gamma-interferon is encapsulated, optionally after concentration or isolation of the liposomes, for example in the ultracentrifuge, are suitable for therapeutic purposes for oral (p.o.) or parenteral (bukkal, lingual, sublingual, i.v., i.c., epicutane, s.c., i.m. or especially nasal) administration.

For oral administration, the liposome-containing aqueous dispersion can be mixed with pharmaceutically acceptable diluents or carriers or with customary additives, for example colorings or flavorings, or can be used in the form of a syrup or in the form of capsules.

For parenteral administration (epicutane) the liposome-containing aqueous dispersion can be mixed with customary thickeners, for example hydroxypropylcellulose, suitable preservatives, antioxidants and perfumes, and can be used in the form of a lotion or a gel for application to the skin or mucous membranes.

For parenteral administration, the aqueous dispersion of the enriched liposomes can be suspended in a suitable carrier liquid, for example sterile, calcuim free, isotonic sodiumchloride or glucose solution, optionally buffered to pH 7.2–7.4.

Based on the present experimental results it is estimated that the highest dose to be applied to a human of about 70 kg weight is about one gram of liposomes containing 200 microgramm of the muramylpeptide (III) and 100,000 units of gamma-interferon, the lowest dose being about 200 mg of liposomes containing 50 microgramm of the muramylpeptide (III) and 1000 units of gamma-interferon. The highest and lowest dose of the encapsulated material, the concentration of the phospholipids in the aqueous phase as well as the proportions of the lipid components (I) and (II) can be varied according to results to be established experimentally in clinical trials.

The pharmaceutical administration system according to the present invention may consist of a "kit of parts" set comprising vials or bottles containing the components (a) and (b) or a mixture of both, and, separately, vials or bottles containing a homogeneous mixture, for example a lyophilisate, of the phospholipids (I) and (II).

The present invention preferably relates to pharmaceutical administration systems consisting of
- (a) a muramylpeptide (III), wherein X represents the group —C(=O)—, $R_1$ is methyl, $R_2$ is hydrogen, $R_3$ is hydrogen or methyl, $R_4$ is methyl, and $R_5$ and $R_6$ is independently of each other represent carbamoyl, carboxy or esterified carboxy, or a pharmaceutically acceptable salt thereof,
- (b) purified, natural or recombinant human gamma interferon,
- (c) a phospholipid of the formula I wherein n, $R_1$, $R_2$ and $Y^\oplus$ are defined as above,
- (d) a phospholipid of the formula II wherein n and $R_1$ to $R_5$ are defined as above, and, optionally, a pharmaceutically acceptable carrier solution buffered from pH 7.2 to 7.4.

The present invention specifically relates to pharmaceutical administration systems consisting of
- (a) sodium-N-acetyl-D-muramyl-L-alanyl-D-isoglutamine or sodium-N-acetyldesmethylmuramyl-L-alanyl-D-isoglutamine of the formula III,
- (b) purified, natural or recombinant human gamma interferon,
- (c) a phospholipid of the formula I wherein n is one, $R_1$ and $R_2$ are acyl each having 10 to 20 carbon atoms and $Y^\oplus$ is the sodium ion,
- (d) a phospholipid of the formula II wherein n is two, $R_1$ and $R_2$ are acyl each having 10 to 20 carbon atoms and $R_3$ to $R_5$ represent hydrogen or methyl, and, optionally, a pharmaceutically acceptable carrier solution buffered from pH 7.2 to 7.4.

The present invention more specifically relates to pharmaceutical administration systems consisting of
- (a) sodium-N-acetyl-D-muramyl-L-alanyl-D-isoglutamine or sodium-N-acetyldesmethylmuramyl-L-alanyl-D-isoglutamine of the formula III,
- (b) purified, natural or recombinant human gamma interferon,
- (c) a synthetic phospholipid of formula I wherein n is one, $R_1$ and $R_2$ are identical $C_{10}$-$C_{20}$-alkenoyl groups, for example 9-cis-hexadecenoyl or 6-cis-, 6-trans-, 9-cis-, 9-trans- or 11-cis-octadecenoyl and $Y^\oplus$ is the sodium ion,
- (d) a synthetic phospholipid of the formula II, wherein $R_1$ and $R_2$ are identical $C_{10}$-$C_{20}$-alkanoyl groups, for example n-dodecanoyl, n-tetradecanoyl, n-hexadecanoyl, or n-octadecanoyl, and $R_3$ to $R_5$ represent methyl, and optionally, a pharmaceutically acceptable carrier solution buffered from pH 7.2 to 7.4.

The invention most specifically relates to pharmaceutical administration systems consisting of
- (a) sodium-N-acetyl-D-muramyl-L-alanyl-D-isoglutamine or sodium-N-acetyldesmethylmuramyl-L-alanyl-D-isoglutamine of the formula III,
- (b) purified, natural or recombinant human gamma interferon,
- (c) synthetic, essentially pure sodium-1,2-di-(9-cis-octadecenoyl)-3-sn-phosphatidyl-(S)-serine (I),
- (d) synthetic, essentially pure 1-n-hexadecanoyl-2-(9-cis-octadecenoyl)-3-sn-phosphatidylcholine (II), and, optionally, a pharmaceutically acceptable carrier solution.

Most preferred is a pharmaceutical administration system consisting of
- (a) 50 to 200 microgramm of sodium-N-acetyl-D-muramyl-L-alanyl-D-isoglutamine or sodium-N-acetyldesmethylmuramyl-L-alanyl-D-isoglutamine of the formula III,
- (b) about 1,000 to 100,000 units of recombinant gamma-interferon having the amino acid sequences:

$H_2N$—Cys—Tyr—Cys—Gln—Asp—Pro—Tyr—Val—Gln—
—Glu—Ala—Glu—Asn—Leu—Lys—Lys—Tyr—Phe—
—Asn—Ala—Gly—His—Ser—Asp—Val—Ala—Asp—
—Asn—Gly—Thr—Leu—Phe—Leu—Gly—Ile—Leu—
—Lys—Asn—Trp—Lys—Glu—Glu—Ser—Asp—Arg—
—Lys—Ile—Met—Gln—Ser—Gln—Ile—Val—Ser—
—Phe—Tyr—Phe—Lys—Leu—Phe—Lys—Asn—Phe—
—Lys—Asp—Asp—Gln—Ser—Ile—Gln—Lys—Ser—
—Val—Glu—Thr—Ile—Lys—Glu—Asp—Met—Asn—
—Val—Lys—Phe—Phe—Asn—Ser—Asn—Lys—Lys—
—Lys—Arg—Asp—Asp—Phe—Glu—Lys—Leu—Thr—
—Asn—Tyr—Ser—Val—Thr—Asp—Leu—Asn—Val—
—Gln—Arg—Lys—Ala—Ile—His—Glu—Leu—Ile—
—Gln—Val—Met—Ala—Glu—Leu—Ser—Pro—Ala—
—Ala—Lys—Thr—Glu—Lys—Arg—Lys—Arg—Ser—
—Gln—Met—Leu—Phe—Gln—Gly—Arg—Arg—Ala—
—Ser—Gln—OH.

or $H_2N$—Cys—Tyr—Cys—Gln—Asp—Pro—Tyr—Val—Lys—
—Glu—Ala—Glu—Asn—Leu—Lys—Lys—Tyr—Phe—
—Asn—Ala—Gly—His—Ser—Asp—Val—Ala—Asp—
—Asn—Gly—Thr—Leu—Phe—Leu—Gly—Ile—Leu—
—Lys—Asn—Trp—Lys—Glu—Glu—Ser—Asp—Arg—
—Lys—Ile—Met—Gln—Ser—Gln—Ile—Val—Ser—
—Phe—Tyr—Phe—Lys—Leu—Phe—Lys—Asn—Phe—
—Lys—Asp—Asp—Gln—Ser—Ile—Gln—Lys—Ser—
—Val—Glu—Thr—Ile—Lys—Glu—Asp—Met—Asn—
—Val—Lys—Phe—Phe—Asn—Ser—Asn—Lys—Lys—
—Lys—Arg—Asp—Asp—Phe—Glu—Lys—Leu—Phe—
—Asn—Tyr—Ser—Val—Thr—Asp—Leu—Asn—Val—
—Gln—Arg—Lys—Ala—Ile—His—Glu—Leu—Ile—
—Gln—Val—Met—Ala—Glu—Leu—Ser—Pro—Ala—
—Ala—Lys—Thr—Gly—Lys—Arg—Lys—Arg—Ser—
—Gln—Met—Leu—Phe—Arg—Gly—Arg—Arg—Ala—
—Ser—Gln—OH and approximately 200 mg to 1,000 mg of
- (c) synthetic essentially pure sodium-1,2-di-(9-cis-octadecenoyl)-3-sn-phosphatidyl-(S)-serine(I), and
- (d) synthetic, essentially pure 1-n-hexadecanoyl-2-(9-cis-octadecenoyl)-3-sn-phosphatidylcholine(II), wherein the molar ratio of the phospholipid component (c) to the phospholipid component (d) is about 30 to 70 mole percent, and optionally, a pharmaceutically acceptable carrier solution.

The pharmaceutical administration systems suitable for application in the form of liposomes are manufactured by preparing a homogeneous mixture of the phospholipids of the formulae I and II and dispersing the homogeneous mixture obtained in an aqueous phase containing a water soluble muramylpeptide in combination with gamma-interferon and, if necessary, buffering the aqueous dispersion to pH 7.0 to 7.8 and, optionally, concentrating and/or separating the liposomes obtained.

The homogeneous mixture of the phospholipids is prepared by formation of a film or a lyophilisate of the phospholipids. The film is prepared by dissolving the phospholipids (I) and (II) in an organic solvent and stripping the solvent.

Suitable solvents are, for example, unsubstituted or substituted, for example halogenated, aliphatic or cycloaliphatic hydrocarbons, for example n-hexane, cyclohexane, methylenechloride, or chloroform, alcohols, for example methanol or ethanol, lower alkanecarboxylic acid esters or amides, for example acetic acid ethylester or dimethylformamide, or ethers, for example diethylether, tetrahydrofurane or dioxane, or mixtures of these solvents.

The organic solvent is subsequently stripped by applying a vacuum, preferably a high vacuum, or by blowing off with an inert gas, for example nitrogen. The lyophilisate is formed by lyophilizing in a conventional manner a solution of the phospholipids (I) and (II) in an organic solvent according to the method as described in the U.S. Pat. No. 4,311,712. Suitable solvents are in the solid form together with the phospholipids (I) and (II) at the temperature of the lyophilisation process and are having a melting point of more than 0° C., for example glacial acetic acid, benzene or dioxane, especially tert-butanol.

A homogeneous mixture also be prepared by spray-drying a solution of the phospholipids (I) and (II) in an organic solvent having a low boiling point such as chloroform. A powder is obtained by this method.

The ratio of the phospholipid component (I) to the phospholipid component (II) in the homogeneous mixture is approximately 10 v. 90 up to 50 v. 50 mole percent. Preferred is the ratio 30 v. 70 mole percent. The approximate ratio of the molar amounts of the encapsulated material (muramyldipeptide in combination with gamma-interferon) divided by the total amount of the phospholipids (I) and (II) is about 0.0001 to 0.1 v. 1.0, preferably 0.005 to 0.01 v. 0.1.

The dispersion is carried out by adding the homogeneous mixture of the phospholipids (I) and (II) to the aqueous phase containing the muramylpeptide (III) and gamma-interferon and by agitation of the aqueous phase (vigorous shaking—Vortex mixer or stirring at high speed). A mixture of small, large, unilamellar or multilamellar liposomes is formed spontaneously at a high rate without supplying external energy. Approximately 0.1 to 40 percent per weight, preferably 2 to 20 percent per weight, of the homogeneous mixture relative to the total weight of the aqueous dispersion can be dispersed in the aqueous phase. Preferably, such dispersions are further diluted to about 1 micromole lipid per ml. The liposome dispersions of that concentration have entrapped approximately 2.5 microliters of the aqueous phase per micromole of the lipid.

The preparation of the pharmaceutical compositions according to the present invention in the form of liposomes can also be carried out by other methods known in the art for preparing liposomes, for example by sonication with supersonic waves, by infusion methods or reversed phase evaporation.

The dispersion step is performed at temperatures below 60°, preferably at room temperature. In view of a potential thermal sensitivity of the encapsulated material, the dispersion is carried out under cooling and, optionally, under inert gas atmosphere, for example nitrogen or argon atmosphere.

The liposomes obtained can be made storage stable in the aqueous phase up to several weeks or months after addition of stabilizers, for example mannite or lactose.

The size of the liposomes formed depends, inter alia, on the structure of the active ingredient and the lipid component, the mixing ratio of the components and the concentration of these components in the aqueous dispersion. Thus, for example, by increasing or reducing the concentration of the lipid component it is possible to produce aqueous phases having a high content of small or large liposomes.

The separation of small liposomes from large liposomes is effected by means of conventional separation methods, for example sedimentation of the large liposomes in an ultracentrifuge, gel filtration or extrusion through straight-pored filters. For example, on centrifuging, for example from 5 to 30 minutes in a rotational field giving rise to an inertial force equivalent to a gravitational field of 5000–40 000×g, large liposomes are deposited, whilst small liposomes remain dispersed and can be decanted off. After repeated centrifugation, complete separation of the large liposomes from the small liposomes is achieved.

Liposomes in the aqueous phase having a diameter greater than $6.0 \times 10^{-8}$ m, for example large multilamellar liposomes, can be separated off by gel filtration, for example with Sepharose or Sephacryl as carriers.

By extrusion through straight-pored filters, for example membrane filters of the Nucleopore ® or polycarbonate type having a pore diameter of approximately $1.0 \times 10^{-7} – 1.0 \times 10^{-9}$ m at a pressure of approximately from 0.1 to 1.5 bar and a filtration rate of approximately 20 ml/h, it is possible to obtain a particularly uniform size distribution of the liposomes.

The formation of liposomes and their content in the aqueous phase can be detected in a manner known per se by using various physical analytical methods, for example by microscopy of freeze-fracture samples and thin sections in an electron microscope, by X-ray defraction, by dynamic light scattering, by mass determination of the filtrate in an analytical ultracentrifuge and, especially, by spectroscopy, for example in the nuclear magnetic resonance spectrum ($^1$H, $^{13}$C and $^{31}$P).

The phospholipids of the formulae I and II are all known. Some of them are commercially available (Avanti, Fluka, Serva). The preparation of 1,2-di-(9-cis-octadecenoyl)-3-sn-phosphatidyl-(S)-serine and of analogous lipids has been described by Browning J. and Seeling J. in Chem. and Phys. of Lipids 24 (1979) 103–118.

The preparation of muramylpeptides of the formula III has been described in the British Patent Specification No. 1,570,625.

The preparation of purified, natural or recombinant, gamma-interferon has been described in the European Patent Application Nos. 63,482, 77,670, 83,777, 88,540, 89,676, 95,350, 99,084, 110,044, 112,976 or 121,157, in the British Patent Specification No. 2,107,718 as well as in the International (PCT) Application Nos. (WO) 83/04053 or WO 84/02129.

The buffer solutions of pH 7,0 to 7,8 preferably are sterile phosphate buffer solutions based on the dihydrogenphosphate/hydrogenphosphate equilibrium ($KH_2PO_4/Na_2HPO_4$). The preparation of these buffer solutions is described in standard manuals, for example "Hager's Handbuch der Pharmazeutischen Praxis", Springer Verlag, Vol. 1, pg. 357–359. Especially sterile, isotonic calcium-free buffer solution of pH 7.2 (Dulbecco) or Hank's Balanced Salt Solution (M.A. Bioproducts, Walkersville Md. USA) is used.

The following examples are illustrating the invention without limiting the scope thereof. Temperatures are given in degrees Celsius.

Further Abbreviations used in the Examples

PC: Phosphatidylcholine
PS: Phosphatidlylserine
r-IFN-γ: Recombinant gamma interferon
HBSS: Hank's balanced salt solution
NCJ: National Cancer Institute
MEM: Eagle's minimum essential medium
FBS: Fetal bovine serum
MDP-D: N-acetyl-D-muramyl-D-alanyl-D-isoglutamine (MDP-D)
PEM: Peritoneal exudate macrophages
NML: Mononuclear Leucocytes
[$^{125}$I]IdUrd: [$^{125}$I]iododeoxyuridine
CMEM: Complete minimum essential medium
N-Rh-PE: N-(lissamine-rhodamine-β-sulfonyl)dioleoylphosphatidylethanolamine
$^{125}$I-phenylpropionyl-PE: N-[3-(3-[$^{125}$I]iodo-4-hydroxybenzyl)propionyl]dipalmitoylphosphatidylethanolamine

EXAMPLE 1

(a) In a round flask 75 mg (95% purity) sodium-1,2-di-(9-cis-octadecenoyl)-3-sn-phosphatidyl-(S)-serine (prepared according to Browning J. and Seelig J., Chem. and Physics of Lipids 24, 103–118 (1979)) and 175 mg (95% purity) 1-n-hexadecanoyl-2-(9-cis-octadecenoyl)-3-sn-phosphatidylcholine (Avanti) are dissolved in 586 mg sterile tert-butanol. The solution is filtered under sterile conditions over Acrodisc ® ($2.0 \times 10^{-7}$ m) and is bottled at −45° in a sterile vial. A vacuum of $6.0 \times 10^{-5}$ bar is applied to the vial until room temperature is reached to remove the solvent.

(b) To this vial containing the lyophilisate of the phospholipids calcium-free, phosphate buffered (pH 7.2–7.4) sodium chloride solution (Dulbecco) containing approximately 50–200 microgramms sodium-N-acetyl-D-muramyl-L-alanyl-D-isoglutamine (British Patent Specification No. 1,570,625) and 1000 to 100,000 units of recombined human immune gamma-interferon obtainable according to European Patent Application No. 121,157 (Kyowa Hakko Kogyo Co.) is added with a sterile syringe. The vial is then shaken on a standardized laboratory mixer (Vortex, state 6). The dispersion containing liposomes is storage stable at 4° and is suitable for parenteral administration (i.v.).

EXAMPLE 2

To the lyophilisate of the phospholipids obtainable according to Example 1(a) 10 ml sterile, calcium-free, phosphate buffered (pH 7.2–7.4) sodium chloride solution (Dulbecco) is added containing a dose of 50 microgramms to 200 microgramms sodium-N-acetyldesmethylmuramyl-L-alanyl-D-isoglutamine and 1000 to 100,000 units of recombinant human gamma interferon. After shaking and aqueous dispersion is suitable for parenteral administration.

EXAMPLE 3.

(a) In a round flask 75 mg (95% purity) sodium-1,2-di-(9-cis-octadecenoyl)-3-sn-phosphatidyl-(S)-serine (prepared according to Browning J. and Seelig J., Chem. and Physics of Lipids 24, 103–118 (1979)) and 175 mg (95% purity) 1-n-hexadecanoyl-2-(9-cis-octadecenoyl)-3-sn-phosphatidylcholine (Avanti) are dissolved in 586 mg sterile tert-butanol. The solution is filtered under sterile conditions over Acrodisc ® ($2.0 \times 10^{-7}$ m) and is bottled at −45° in a sterile vial. The vial is rotated with 150 rpm and the solvent is blown off in a stream of dry, purified and filtered nitrogen. A vacuum of $6.0 \times 10^{-5}$ bar is applied to the vial which is then sealed under argon inert gas atmosphere.

(b) To this vial containing a film of the phospholipids 10 ml sterile, calcium-free, phosphate buffered (pH 7.2–7.4) sodium chloride solution (Dulbecco) containing approximately 50–200 microgramms sodium-n-acetyl-D-muramyl-L-alanyl-D-isoglutamine (British Patent Specification No. 1,570,625) and 1000 to 100,000 units of recombinant human immune gamma-interferon obtainable according to European Patent Application No. 121,157 (Kyowa Hakko Kogyo Co.) is added with a sterile syringe. The vial is then shaken on a standardized laboratory mixer (Vortex, stage 6). The dispersion containing liposomes is storage stable at 4° and is suitable for parenteral administration (i.v.).

EXAMPLE 4

To the thin film of the phospholipids obtainable according to Example 3(a) 10 ml sterile, calcium-free phosphate buffered (pH 7.2–7.4) sodium chloride solution (Dulbecco) is added containing a dose of 50 microgramm to 200 microgramm sodium-N-acetyldesmethylmuramyl-L-alanyl-D-isoglutamine and 1000 to 100,000 units of recombinant humane gamma interferon. After shaking the aqueous dispersion is suitable for parenteral administration.

EXAMPLE 5

MLV are prepared from a mixture of chromatographically pure distearoyl-PC and PS in a molar ratio of 7:3, MDP and r-IFN-γ and, for the purpose of testing, MDP and separately r-IFN-γ are encapsulated within the MLV in a conventional manner according to Example 3 by mechanical agitation on a Vortex mixer. Unencapsulated materials are removed by washing the MLV by centrifugation. The internal aqueous volume of the MLV is determined to be 2.5±0.4 μl/μmol of the phospholipid. The liposome preparations are adjusted to 1 μmole total lipid/ml in media. Control MLV (containing HBSS) or MLV containing MDP, r-IFN-γ or both are added to the macrophage monolayer at a liposome concentration of 100 nmoles phospholipid per $10^5$ cells. This dose of MLV contains approximately 0.25 μl of encapsulated materials, and should be compared with the 200 μl (volume of media in each well) of free materials necessary to induce macrophage activation. The dose of free materials or that of MLV containing agents used routinely to render macrophages tumoricidal is not directly toxic to the target cells.

This liposome dispersion is suitable for testing as exemplified in the following Test Reports:

TEST REPORT I

A-Materials and Methods

Animals

Specific-pathogen free mice of the inbred C57BL/6N strain, 8 to 10 weeks old from the NCI-Frederick Cancer Research Facility's Animal Production Area were used.

Reagents

RPMI 1640 medium, MEM, HBSS, human AB serum, and FBS were obtained from M.A. Bioproducts, Walkersville, MD. Recombinant mouse gamma interferon and r-IFN-γ were obtained from Genentech, Inc., South San Francisco, CA. Sodium iodoacetate and MDP-D were obtained from Sigma Chemical Co., Ltd. (St. Louis, MO). Pronase (from *Streptomyces griseus*) was obtained from Calbiochem (Los Angeles, CA). All reagents were free of endotoxins as determined by the Limulus amebocyte lysate assay (sensitivity limit of 0.125 ng/ml (Associates of Cape Cod, MA)).

Cell cultures

The B16-BL6 tumor cell line, originated from the B16 melanoma syngeneic to the C57BL/6 mice, was obtained by an in vitro selection procedure for invasion (J. R. Hart, Am. J. Pathol. 97, 587 (1979)). The cultured cell line, A 375, derived from a human melanoma, was used as human tumor target cells. The mouse and human melanoma cells were maintained as monolayer cultures in Eagle's MEM supplemented with 5% FBS, vitamin solution, sodium pyruvate, nonessential amino acid, and L-glutamine (M.A. Bioproducts, Walkersville, MD). Cultures were incubated at 37° C. in a humidified atmosphere containing 5% $Co_2$. All cultures were free of mycoplasma and pathogenic mouse viruses.

Collection and cultivation of mouse PEM

PEM were collected by peritoneal lavage from mice given i.p. injections of 2 ml thioglycollate broth (Baltimore Biological Laboratories, Cockeysville, MD) 4 days before harvest (Raz A. et al. Cancer Immunol. Immunother. 7, 157 (1979). The PEM were centrifuged at 250×g for 10 min, resuspended in serum-free medium, and plated into Microtest II plastic tissue culture dishes ($10^5$ PEM per well of 38 $mm^2$ surface area). After incubation for 40 min at 37° C., the wells were rinsed with HBSS to remove nonadhering cells and processed as described below. The resultant monolayers of macrophages were >98% pure according to morphologic and phagocytic criteria.

Isolation and culture of human peripheral blood monocytes

Peripheral blood monocytes were isolated from MNL on a preformed continuous Percoll gradient and adherence as described by J. R. Hester et al. Blood 54: 254–262 (1969). $1 \times 10^5$ monocytes were added to each well of flat-bottom Microtest II plates and were allowed to adhere for 1 h at 37° C. Nonadherent cells were removed by three washes with RPMI 1640 medium. At this point, the purity of the monocyte monolayer was >b 97%, as assessed by the following criteria: India ink ingestion, morphology, nonspecific esterase staining, and the ability to stain the cells with monoclonal antihuman monocyte antibody 61D3 (Bethesda Research Laboratories, Inc.)

In vitro activation of macrophages/monocytes

Purified cultures of mouse PEM or human blood monocytes were incubated at 37° C. for 18–24 h with 0.2 ml of control medium, with MLV containing either human r-IFN-γ and MDP or mouse r-IFN-γ and MDP, or with control preparations of MLV, i.e. MLV containing HBSS and suspended in medium with free r-IFN-γ and MDP at dose level identical to that captured within the MLV. After the incubation period, the monocyte or macrophage cultures were thoroughly washed and $10^4$ [$^{125}$I]IdUrd-labled target cells were added as described below.

In vitro assays of monocyte-macrophage mediated cytotoxicity

Macrophage or monocyte mediated cytotoxicity was assessed by a radioactive release assay as described in Pabst M. J. and Johnston R. B. Jr. J. Exp. Med. 151, 101 (1980). Target cells in exponential growth phase were incubated for 24 h in medium supplemented with [$^{125}$I]IdUrd (0.2 μCi/ml; specific activity, 200 mCi/mmol; New England Nuclear, Boston, MA). The cells then were washed 3 times with warm HBSS to remove unbound radiolabel, harvested by a short trypsinization (0.25% Difco trypsin and 0.02% EDTA for 1 min at 37°), and resuspended in CMEM $1 \times 10^4$. Viable cells were plated into the wells containing macrophages to achieve a population density of 2500 macrophages and 250 tumor cells per sq mm (or an initial macrophage:target cell ratio of 10/1). At this population density, normal (untreated) macrophages are not cytotoxic to neoplastic cells. No significant differences were detected in the plating efficiency (binding) of [$^{125}$I]IdUrd-labled target cells to control or liposome-treated macrophage populations. Radiolabeled target cells also were plated alone as in additional control group. The macrophage-target cell cultures were refed with medium 24 h after the addition of the target cells to remove all nonplated cells and then were incubated for up to 3 days at 37°. At this time, the cultures were washed twice with HBSS to remove adherent cells, and the remaining viable, adherent cells were lysed with 0.1 ml of 0.1N NaOH. The lysate was absorbed in a cotton swab and placed directly into $10 \times 75$ mm tubes; radioactivity was measured in a gamma counter. Maximal in vitro macrophage-mediated cytotoxicity in this assay was obtained after 3 days of incubation with target cells, and macrophages did not reincorporate [$^{125}$I]IdUrd released from dead target cells. The cytotoxic activity of the macrophages was calculated as follows:

$$\% \text{ Cytotoxicity} = \frac{\substack{\text{(cpm in target cells cultured} \\ \text{with normal macrophages)} - \\ \text{(cpm in target cells cultured} \\ \text{with test macrophages)}}}{\substack{\text{cpm in target cells cultured} \\ \text{with normal macrophages}}} \times 100$$

Experimental results were analyzed for their statistical significance by Student's 2-tailed t test.

Phagocytosis of liposomes

To assay phagocytosis of MLV by macrophages, N-Rh-PE was prepared by reacting lissamine rhodamine-B-sulfonylchloride (Molecular Probes, Plano, TX) with dipalmitoylphosphatidylethanolamine. $^{125}$I-phenylpropionyl-PE was also prepared by using $^{125}$I-Bolton-Hunter reagent (specific activity 2000 Ci/mmol, New England Nuclear, Boston, MA). MLV containing N-Rh-PE and $^{125}$I-phenylpropionyl-PE were prepared by the same methods as mentioned above.

Macrophage binding and phagocytosis of liposomes were assessed by incubating adherent macrophages with MLV (100 nmoles lipid per $10^5$ macrophages) containing trace amounts of $^{125}$I-phenylpropionyl-PE and N-Rh-PE for different time periods. The monolayers were extensively washed with HBSS and the cells were lysed with 0.1N NaOH. Radioactivity in the lysates was monitored in a gamma counter.

TABLE 1

B Results
In-vitro Activation of Mouse Macrophages or Human Monocytes by Recombinant Mouse or Human Interferon-gamma Encapsulated in Liposomes with Muramyl Dipeptide.

| Treatment of mouse macrophages with liposomes containing[a]: | | | Percent macrophage mediated cytolysis against B16 melanoma[b] | Treatment of human monocytes with liposomes containing[a]: | | | Percent monocyte mediated cytolysis against A375 melanoma[b] |
|---|---|---|---|---|---|---|---|
| r-IFN-γ Source | Units/ml | MDP ng/ml | | r-IFN-γ Source | Units/ml | MDP ng/ml | |
| Mouse | 2 | — | 2% | Human | 0.2 | — | 10% |
| Mouse | 2 and | 0.2 | 30%[c] | Human | 0.2 and | 0.2 | 41%[c] |
| Human | 2 | — | 1% | Mouse | 2 | — | 6% |
| Human | 2 and | 0.2 | 23%[c] | Mouse | 2 and | 0.2 | 45%[c] |
| — | | 0.2 | −4% | — | | 0.2 | 4% |
| MLV containing HBSS suspended in 2 U mouse r-IFN-γ and 0.2 ng MDP | | | −6% | MLV containing HBSS suspended in 0.2 U human r-IFN-γ and 0.2 ng MDP | | | 0% |
| MLV containing HBSS suspended in 0.2 U human r-IFN-γ and 0.2 ng MDP | | | −2% | MLV containing HBSS suspended in 2 U mouse r-IFN-γ and 0.02 ng MDP | | | 3% |

TABLE 2

Activation of Tumoricidal Properties in Untreated or Pronase Treated Human Blood Monocytes by Liposome Encapsulated Recombinant Human Interferon-gamma and Muramyl Dipeptide.

| | Radioactivity in viable target cells on day 3 of cocultivation with human monocytes treated with: | |
|---|---|---|
| Monocytes activated with[a]: | Medium | Pronase (10 μg) |
| No monocytes, tumor cells alone | 667 ± 17[b] | |
| Medium | 568 ± 40 | 581 ± 33 |
| MLV containing r-IFN-γ (0.2 U) and MDP (0.2 ng) | 272 ± 41 (52%) | 283 ± 19 (51%) |
| MLV containing HBSS suspended in free r-IFN-γ (0.2 U) and MDP (0.2 ng) | 560 ± 33 | 586 ± 43 |
| MLV containing MDP (2 μg) | 328 ± 59 (42%)[c] | 313 ± 49 (46%)[c] |

Footnotes for Table 2
[a] $10^5$ human blood monocytes were treated with pronase for 10 min at 37° C. in serum free medium. The treated and control monocytes were washed twice and incubated for 8 h with MLV containing these agents. The cultures were then washed and incubated in medium for additional 16 hours. $10^4$ [$^{125}$I] IdUrd labeled A375 melanoma cells were added to the macrophage monolayers. The cultures were terminated after 72 h of cocultivation.
[b] mean cpm ± S.D. of triplicate cultures.
[c] Number in parentheses is percent macrophage mediated cytotoxicity as compared with appropriate control macrophages at identical density. $p < 0.001$.

TEST REPORT II

A-Materials and Methods

Reagents

MEM, Roswell Park RPMI 1640, HBSS ($Ca^{2+}$- and $Mg^{2+}$-free), human AB serum, FBS, and components were obtained from M.A. Bioproducts, Walkersville, MD. Human r-IFN-γ was obtained from Genentech, Inc., South San Francisco, CA. All the reagents and media used in this study were endotoxin-free (detection limit of <0.125 ng/ml), as determined by the Limulus amebocyte lysate assay (Associates of Cape Cod, Inc., Woods Hole, MA).

Target cell culture

The A375 line which was derived from a human melanoma, was adapted to growth in culture as described by I. J. Fidler and E. S. Kleinermann in J. Clin. Oncol. 2(8), 837–943, 1984. The cell line was free of Mycoplasma and was maintained on plastic in Eagles' MEM supplemented with sodium pyruvate, vitamins, L-glutamine, nonessential amino acids, and 10% head-inactivated FBS at 37° C. in a humidified atmosphere containing 5% $CO_2$. Cytotoxicity assays were performed when the cultured target cells were in their exponential growth phase.

Isolation and culture of human peripheral blood monocytes.

Mononuclear cells were obtained from incidental samples derived from collections of platelet concentrates using an IBM 2997 blood-cell separator (Pace J. L. et al. Proc. Natl. Acad. Sci. USA 80, 3782–3786, 1983) Monocytes were isolated from the mononuclear cell sample by centrifugal elutriation using a JE-6B Beckman elutriation rotor as described by Lopez-Berestein et al. in J. Immunol. 130, 1500–1504, 1093.

A fraction that contained more than 90% of the total monocyte population was obtained at a speed at 3000 rpm and a flow rate of 41 ml/min. These cells were greater than 95% of the monocytes as determined by nonspecific esterase staining and morphological examination, and were more than 97% viable as determined by the trypan blue dye exclusion. The fraction was pooled, washed twice with HBSS, and resuspended in RPMI 1640 supplemented with 5% human AB serum to a concentration of $5 \times 10^5$ monocytes/ml. These cells were plated into 38-mm$^2$ well (96-well Microtest II plate, Flow Laboratories, McLean, VA). After a 2 h incubation, the non-adherent cells were removed by vigorous washing with medium. At this point, the purity of monocytes was greater than 99% as assessed by the examination of cell morphology, phagocytosis, and nonspecific esterase staining.

In vitro activation of monocytes by liposome-encapsulated activating agents

Monocytes were incubated in media with MLV containing r-IFN-γ or MDP or both for 18–24 h at 37° C. Controls always included MLV containing HBSS suspended in medium with free-activating agents. The monocyte cultures were rinsed thoroughly with media before the addition of radiolabeled target cells.

Monocyte-mediated cytotoxicity

Cytotoxicity was assessed by measuring the release of radioactivity as described by Kleinermann E. S. et al. in J. Clin. Invest. 72, 304–315, 1983 and in Cancer Res. 44, 4470–4475, 1984. Target cells in their exponential growth phase, were incubated in the appropriate medium which contained [$^{125}$I]IdUrd (0.3 μCi/ml; specific activity greater than 2000 Ci/mmol; New England Nuclear; Boston MA) for 24 h. The cells were than washed twice to remove unbound radioiodine, harvested by a 1-min trypsinization (0.25% Difco trypsin, 0.02% EDTA), and washed. The labeled cells were resuspended in RPMI 1640 supplemented with 5% FBS and $1 \times 10^4$ cells were plated into the 38-mm$^2$ culture wells to produce an intial target-to-effector cell ratio of 1:10. Radiolabeled cells were also plated alone as an additional control group. After 16 h the cultures were washed to remove the nonadherent cells and refed with fresh medium. After 72 h of cocultivation, the cultures were washed twice with HBSS and the adherent, viable cells were lysed with 0.1 ml of 0.1N NaOH. The radioactivity of the lysate was monitored in a gamma counter.

The percentage of generated cytotoxicity mediated by activated human monocytes was calculated as follows:

$$\text{Percentage of cytotoxicity mediated by activated monocytes} = \frac{A - B}{A} \times 100$$

wherein A represents cpm in cultures of control monocytes and target cells, and B represents cpm in cultures of activated monocytes and target cells.

Statistical analysis

The statistical significance of differences between test groups was analyzed by Student's t test (two-tailed).

B-Results

TABLE

Synergistic Activation of Tumoricidal Properties in Human Blood Monocytes by MDP and Human r-IFN-γ Encapsulated in Liposomes

| Treatment of monocytes[a] | Radioactivity in viable target cells on day 3[b] |
|---|---|
| MLV containing r-IFN-γ (0.2 U) | 1232 ± 154 |
| MLV containing r-IFN-γ (0.02 U) | 1292 ± 108 |
| MLV containing MDP (0.1 ng) | 1211 ± 94 |
| MLV containing MDP (0.02 ng) | 1195 ± 68 |
| MLV containing r-IFN-γ (0.2 U) and MDP (0.02 ng) | 587 ± 50 (52%)[c] |
| MLV containing r-IFN-γ (0.02 U) and MDP (0.02 ng) | 1147 ± 166 |
| MLV containing r-IFN-γ (0.2 U) and MLV containing MDP (0.02 ng) | 792 ± 48 (30%)[c] |
| MLV containing r-IFN-γ (0.02 U) and MLV containing MDP (0.02 ng) | 1301 ± 90 |

Footnotes for Table:
[a] $10^5$ monocytes were plated into 38 mm$^2$ culture cells and incubated as indicated for 18-24 h at 37° C. MLV preparations were used at a concentration of 100 nmoles of total phospholipids per $10^5$ cells. After washing the cultures thoroughly, $10^4$ [$^{125}$I] IdUrd-labeled target cells were added. Cytotoxicity was determined after 72 h of cocultivation.
[b] Mean cpm ± SD of triplicate cultures.
[c] Number in parentheses is the percentage of cytotoxicity compared with control macrophages at corresponding ratio (density) to target cells. P < .005.

The incubation of monocytes with endotoxin-free medium, with 100 nmol of MLV containing 0.02 U or 0.2 U of r-IFN-γ, with 100 nmol of MLV containing 0.02 ng or 0.1 ng of MDP, did not produce their activation for tumor cytolysis. In contrast, the incubation of monocytes with 100 nmol MLV containing subthreshold doses of r-IFN-γ (0.2 U) and MDP (0.02 ng) resulted in synergistic activation of blood monocytes (52%, P<0.005). The delivery of r-IFN-γ to monocytes in one MLV preparation and MDP in another also produced activation of antitumor properties, albeit at a reduced level (30% cytotoxicity, P<0.005). The activation of blood monocytes by r-IFN-γ and MDP required that both agents be delivered intracellularly. Monocytes incubated with 100 nmol of MLV containing HBSS within the aqueous interior and suspended in medium containing the entrapped dose of r-IFN-γ (0.2 U) and MDP (0.2 ng) were not rendered tumoricidal.

What is claimed is:

1. A pharmaceutical administration system consisting of
(a) a water soluble muramylpeptide,
(b) gamma-interferon,
(c) a phospholipid of the formula

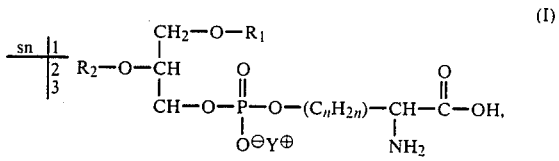

wherein n is one, two or three, $R_1$ and $R_2$ independently of each other represent alkyl, alkenyl or acyl each having 10-20 carbon atoms, and $Y^\oplus$ is the cation of a pharmaceutically acceptable base,
(d) a phospholipid of the formula

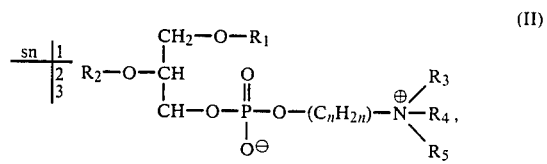

wherein n is two, three or four, $R_1$ and $R_2$ are defined as above and $R_3$, $R_4$ and $R_5$ represent hydrogen or $C_1$-$C_4$-alkyl, and, optionally, a pharmaceutically acceptable carrier solution buffered to pH 7.0-7.8, and, optionally a pharmaceutically acceptable carrier in solid form.

2. A pharmaceutical administration system according to claim 1 consisting of
(a) a muramylpeptide of the formula

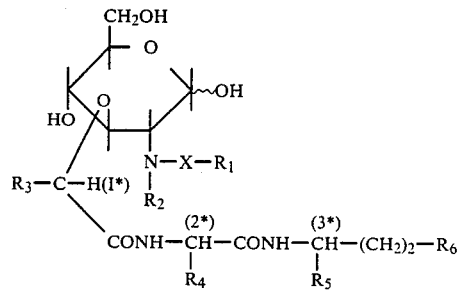

wherein X represents the groups —C(=O)— or —C(=O)—O—; $R_1$ represents $C_1$-$C_4$-alkyl; $R_2$, $R_3$ and $R_4$ indpendently of each other represent or $C_1$-$C_4$-alkyl; $R_5$ and $R_6$ independently of each other represent carbamoyl, carboxy or esterified carboxy; when $R_3$ is other than hydrogen, the configuration about the carbon atom designated (I*) is D; when $R_4$ is other than hydrogen the configuration about the carbon atom designated (2*) is L; and when $R_5$ is other than hydrogen the configuration about the carbon atom designated (3*) is D; or a pharmaceutically acceptable salt thereof,
(b) purified, natural or recombinant human gamma interferon,
(c) a phospholipid of the formula I wherein n, $R_1$, $R_2$ and $Y^\oplus$ are defined as above,
(d) a phospholipid of the formula II wherein n and $R_1$ to $R_5$ are defined as above, and, optionally, a pharmaceutically acceptable carrier solution buffered from pH 7.2 to 7.4.

3. A pharmaceutical administration system according to claim 1 consisting of
   (a) sodium-N-acetyl-D-muramyl-L-alanyl-D-isoglutamine or sodium-N-acetyldesmethylmuramyl-L-alanyl-D-isoglutamine,
   (b) purified, natural or recombinant human gamma interferon,
   (c) a phospholipid of the formula I wherein n is one, $R_1$ and $R_2$ are acyl each having 10 to 20 carbon atoms and $Y^\oplus$ is the sodium ion,
   (d) a phospholipid of the formula II wherein n is two, $R_1$ and $R_2$ are acyl each having 10 to 20 carbon atoms, and $R_3$ to $R_5$ represent hydrogen or methyl, and, optionally, a pharmaceutically acceptable carrier solution buffered from pH 7.2 to 7.4.

4. A pharmaceutical administration system according to claim 1 consisting of
   (a) sodium-N-acetyl-D-muramyl-L-alanyl-D-isoglutamine or sodium-N-acetyldesmethylmuramyl-L-alanyl-D-isoglutamine,
   (b) purified, natural or recombinant human gamma interferon,
   (c) a synthetic phospholipid of the formula I wherein n is one, $R_1$ and $R_2$ are identical $C_{10}$-$C_{20}$-alkenoyl groups and $Y^\oplus$ is the sodium ion,
   (d) a synthetic phospholipid of the formula II, wherein $R_1$ and $R_2$ are identical $C_{10}$-$C_{20}$-alkanoyl groups and $R_3$ to $R_5$ represent methyl, and, optionally, a pharmaceutically acceptable carrioer solution buffered from pH 7.2 to 7.4.

5. A pharmaceutical administration system according to claim 1 consisting of
   (a) sodium-N-acetyl-D-muramyl-L-alanyl-D-isoglutamine or sodium-N-acetyldesmethylmuramyl-L-alanyl-D-isoglutamine,
   (b) purified, natural or recombinant, human gamma-interferon,
   (c) synthetic, essentially pure sodium-1,2-di-(9-cis-octadecenoyl)-3-sn-phosphatidyl-(S)-serine (I),
   (d) synthetic, essentially pure 1-n-hexadecanoyl-2-(9-cis-octadecenoyl)-3-sn-phosphatidylcholine (II), and, optionally, a pharmaceutically acceptable carrier solution.

6. A pharmaceutical administration system according to claim 1 consisting of
   (a) 50 to 200 microgramm of sodium-N-acetyl-D-muramyl-L-alanyl-D-isoglutamine or sodium-N-acetyldesmethylmuramyl-L-alanyl-D-isoglutamine,
   (b) about 1,000 to 100,000 units of recombinant gamma-interferon having the amino acid sequences:

$H_2N$—Cys—Tyr—Cys—Gln—Asp—Pro—Tyr—Val—Gln—
—Glu—Ala—Glu—Asn—Leu—Lys—Lys—Tyr—Phe—
—Asn—Ala—Gly—His—Ser—Asp—Val—Ala—Asp—
—Asn—Gly—Thr—Leu—Phe—Leu—Gly—Ile—Leu—
—Lys—Asn—Trp—Lys—Glu—Glu—Ser—Asp—Arg—
—Lys—Ile—Met—Gln—Ser—Gln—Ile—Val—Ser—
—Phe—Tyr—Phe—Lys—Leu—Phe—Lys—Asn—Phe—
—Lys—Asp—Asp—Gln—Ser—Ile—Gln—Lys—Ser—
—Val—Glu—Thr—Ile—Lys—Glu—Asp—Met—Asn—
—Val—Lys—Phe—Phe—Asn—Ser—Asn—Lys—Lys—
—Lys—Arg—Asp—Asp—Phe—Glu—Lys—Leu—Thr—
—Asn—Tyr—Ser—Val—Thr—Asp—Leu—Asn—Val—
—Gln—Arg—Lys—Ala—Ile—His—Glu—Leu—Ile—
—Gln—Val—Met—Ala—Glu—Leu—Ser—Pro—Ala—
—Ala—Lys—Thr—Glu—Lys—Arg—Lys—Arg—Ser—
—Gln—Met—Leu—Phe—Gln—Gly—Arg—Arg—Ala—
—Ser—Gln—OH, or $H_2N$—Cys—Tyr—Cys—Gln—Asp—Pro—Tyr—Val—Lys—
—Glu—Ala—Glu—Asn—Leu—Lys—Lys—Tyr—Phe—
—Asn—Ala—Gly—His—Ser—Asp—Val—Ala—Asp—
—Asn—Gly—Thr—Leu—Phe—Leu—Gly—Ile—Leu—
—Lys—Asn—Trp—Lys—Glu—Glu—Ser—Asp—Arg—
—Lys—Ile—Met—Gln—Ser—Gln—Ile—Val—Ser—
—Phe—Tyr—Phe—Lys—Leu—Phe—Lys—Asn—Phe—
—Lys—Asp—Asp—Gln—Ser—Ile—Gln—Lys—Ser—
—Val—Glu—Thr—Ile—Lys—Glu—Asp—Met—Asn—
—Val—Lys—Phe—Phe—Asn—Ser—Asn—Lys—Lys—
—Lys—Arg—Asp—Asp—Phe—Glu—Lys—Leu—Phe—
—Asn—Tyr—Ser—Val—Thr—Asp—Leu—Asn—Val—
—Gln—Arg—Lys—Ala—Ile—His—Glu—Leu—Ile—
—Gln—Val—Met—Ala—Glu—Leu—Ser—Pro—Ala—
—Ala—Lys—Thr—Gly—Lys—Arg—Lys—Arg—Ser—
—Gln—Met—Leu—Phe—Arg—Gly—Arg—Arg—Ala—
—Ser—Gln—OH, and approximately 200 mg to 1,000 mg of
   (c) synthetic, essentially pure sodium-1,2-di-(9-cis-octadecenoyl)-3-sn-phosphatidyl-(S)-serine(I) and
   (d) synthetic, essentially pure 1-n-hexadecanoyl-2-(9-cis-octadecenoyl)-3-sn-phosphatidylcholine (II), wherein the molar ratio of the phospholipid component (c) to the phospholipid component (d) is about 30 to 70 mole percent, and, optionally, a pharmaceutically acceptable carrier solution.

7. A method of stimulating the immune system in humans or animals which comprises administering to a human or animal in need of such administration an effective amount of a pharmaceutical administration system as claimed in claim 1.

8. A method of activating macrophages or monocytes in humans which comprises administering to a human in need of such administration an effective amount of a pharmaceutical administration system as claimed in claim 1.

* * * * *